(12) United States Patent
Kullik et al.

(10) Patent No.: US 7,066,913 B2
(45) Date of Patent: Jun. 27, 2006

(54) ANESTHETIC METERING SYSTEM

(75) Inventors: Götz Kullik, Lübeck (DE); Jochim Koch, Ratzeburg (DE)

(73) Assignee: Dräger Medical AG & Co. KGaA, Lübeck (DE)

(*) Notice: Subject to any disclaimer, the term of this patent is extended or adjusted under 35 U.S.C. 154(b) by 843 days.

(21) Appl. No.: 10/102,474

(22) Filed: Mar. 20, 2002

(65) Prior Publication Data

US 2002/0157670 A1     Oct. 31, 2002

(30) Foreign Application Priority Data

Apr. 28, 2001  (DE) ................................ 101 21 004

(51) Int. Cl.
*A61M 5/155* (2006.01)
(52) U.S. Cl. .................... 604/246; 604/23; 128/205.13
(58) Field of Classification Search ................ 604/131, 604/132, 133, 251, 252, 253, 254, 246, 186, 604/207, 23; 128/200.11, 200.24
See application file for complete search history.

(56) References Cited

U.S. PATENT DOCUMENTS

| | | | | |
|---|---|---|---|---|
| 2,850,211 A | * | 9/1958 | Fernandez | 222/67 |
| 4,265,241 A | * | 5/1981 | Portner et al. | 604/131 |
| 4,554,927 A | * | 11/1985 | Fussell | 600/483 |
| 5,197,462 A | * | 3/1993 | Falb et al. | 128/203.14 |
| 5,293,865 A | * | 3/1994 | Altner et al. | 128/203.12 |
| 5,840,071 A | * | 11/1998 | Kriesel et al. | 604/132 |
| 6,083,189 A | * | 7/2000 | Gonon et al. | 604/19 |

FOREIGN PATENT DOCUMENTS

| EP | 0121255 A2 | * | 3/1984 |
|---|---|---|---|
| EP | 0 449 545 A1 | | 10/1991 |

* cited by examiner

*Primary Examiner*—Nicholas D. Lucchesi
*Assistant Examiner*—Melissa A. McCorkle
(74) *Attorney, Agent, or Firm*—McGlew & Tuttle, P.C.

(57) ABSTRACT

An anesthetic metering system includes an anesthetic reservoir (1) having an anesthetic reserve (2), which is limited by a flexible material wall and to which pressure is admitted by means of a propellant (3) acting thereon via the wall material. The anesthetic reservoir (1) has a first valve (4), which is in flow connection with the liquid anesthetic reserve (2) and can be inserted into a mounting element (6) of an anesthesia apparatus. The metered release of anesthetic to the anesthesia apparatus takes place via a volumetric nozzle (8). The present invention provides an anesthetic metering device which avoids, on the one hand, the drawbacks of the anesthetic evaporators used previously, which are to be refilled with anesthetics at the workplace, and makes possible the refilling of the anesthetic reservoir (1) at the anesthetic manufacturer, on the other hand.

20 Claims, 1 Drawing Sheet

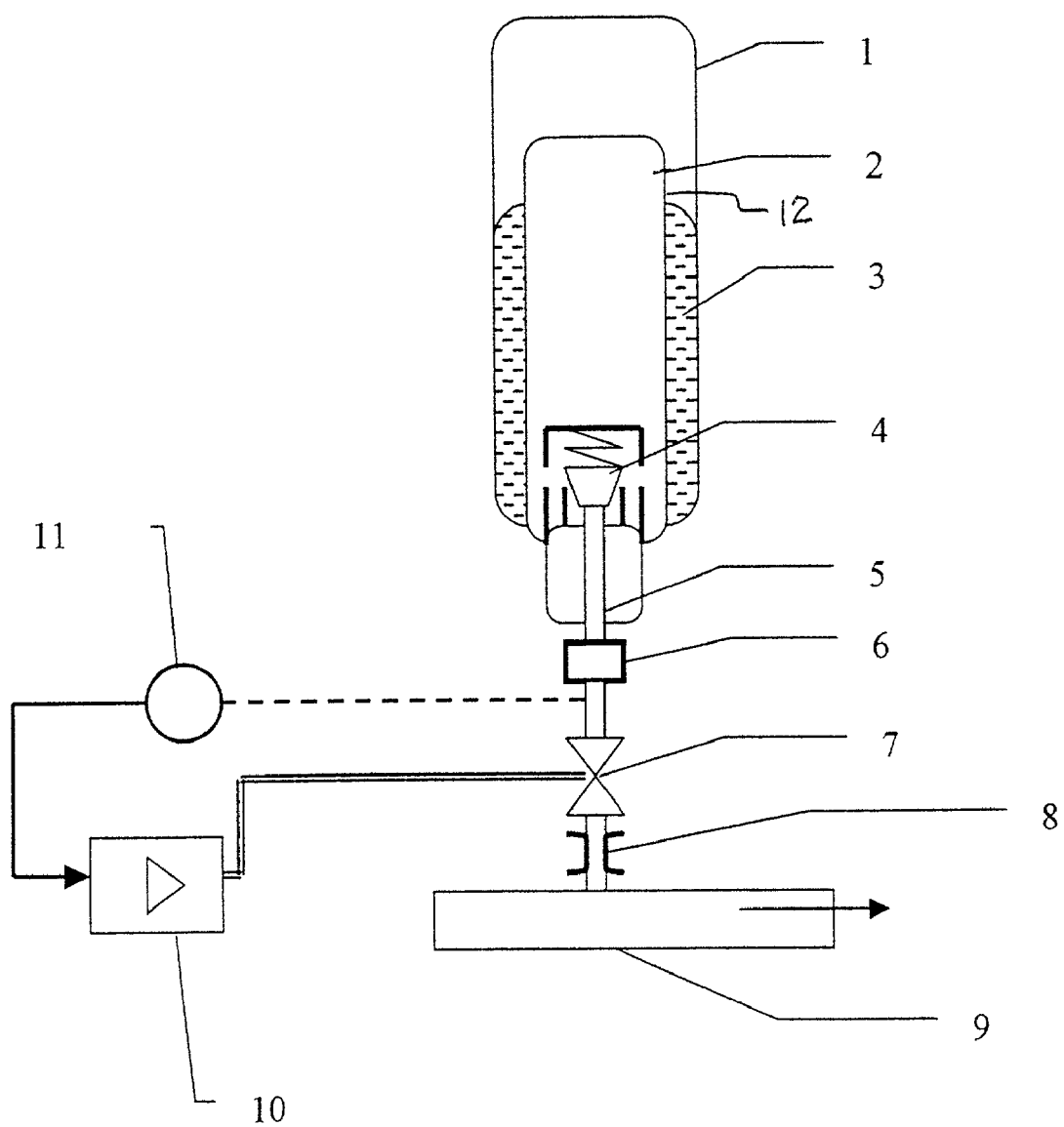
Fig. 1

ANESTHETIC METERING SYSTEM

CROSS REFERENCE TO RELATED APPLICATIONS

This application claims the benefit of priority under 35 U.S.C. § 119 of German Patent Application DE 101 21 004.3-44 filed Apr. 28, 2001.

FIELD OF THE INVENTION

The present invention pertains to an anesthetic metering system, method and device with an anesthetic reservoir having a liquid anesthetic reserve.

BACKGROUND OF THE INVENTION

Prior-art anesthetic metering systems, e.g., that described in EP 0 449 545 A1, have, in general, an anesthetic evaporator with an associated reservoir with a liquid anesthetic reservoir. Such reservoirs are usually installed permanently at the anesthetic evaporator and are refilled according to relatively complicated and time-consuming techniques with a filling tube, a filling adapter or a funnel. The fact that part of the anaesthetic added during refilling is easily spilled and unintendedly burdens the persons present due to evaporation into the ambient air is especially disadvantageous.

SUMMARY OF THE INVENTION

Therefore, the object of the present invention is to provide an improved anesthetic metering system, which overcomes the drawbacks of the prior-art systems, on the one hand, and additionally makes it possible to refill the anesthetic reservoir at the anesthetic manufacturer.

According to the invention, an anesthetic metering system is provided with an anesthetic reservoir having an anesthetic reserve, which is limited by means of a flexible wall material and to which pressure is admitted by means of an propellant acting thereon via the wall material. The anesthetic reservoir has a first valve, which is in flow connection with the liquid anesthetic reserve, and can be inserted into a mounting element of an anesthesia apparatus. The metered release of anesthetic to the anesthesia apparatus takes place via a volumetric nozzle.

One essential advantage of the subject according to the invention follows from the use of an anesthetic reservoir, into which a propellant is admitted and has a liquid anesthetic reserve separated by a flexible partition. Due to the cooperation of the anesthetic reservoir designed as described with the components of an anesthesia apparatus according to the invention, an anesthetic metering system is created, which makes it possible to rapidly change used anesthetic reservoirs and to refill these reservoirs at the anesthetic manufacturer. The hitherto usual complicated filling of the reservoirs of anesthetic evaporators at the clinical workplace, which is potentially hazardous to the health of the workers, is eliminated due to the anesthetic metering system according to the present invention.

The anesthesia apparatus may have a second valve, which is in flow connection with the mounting element. This is actuated via a measuring and control unit as a function of the anesthetic currently being used and as a function of the pressure measured by means of a pressure pickup in front of the second valve. As an alternative or in addition, this is actuated via a measuring and control unit as a function of the temperature of the liquid anesthetic being used for metering the anesthetic, which is measured by means of a temperature sensor.

Preferred propellants include heptafluoropropane or nitrogen.

The flexible wall material that limits the liquid anesthetic reserve may consist of aluminum, polyethylene or a metal-coated flexible plastic laminate.

The first valve may be a valve that is opened mechanically or electromagnetically during insertion into the anesthesia apparatus.

The anesthetic reservoir may be provided with a code in the form of a transponder or an electronic memory element. This can be read by the anesthesia apparatus and is specific to the anesthetic and/or the anesthetic reservoir.

The anesthetic reservoir may be equipped with a filling level sensor for the remaining anesthetic reserve. This sensor signal may be processed and/or displayed in the anesthesia apparatus.

The pressure pickup may be a piezo crystal pickup. At least one heating means for heating the anesthetic may be arranged at the anesthesia apparatus.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE schematically shows the components needed to embody the present invention.

DESCRIPTION OF THE PREFERRED EMBODIMENTS

Referring to the drawings in particular, a pressure-resistant anesthetic reservoir 1, made especially of aluminum, has a liquid anesthetic reserve 2 limited by means of an impermeable, flexible material wall 12. The flexible material wall 12 consists especially of aluminum, polyethylene or a metal-coated, flexible plastic laminate, which must be resistant to the anesthetic being used on the inside and to the propellant 3 used on the outside. The anesthetic reserve 2 and the propellant 3 are separated by the wall 12 defining a propellant space separate from the anesthetic reserve. The propellant 3 pressurizes the anesthetic via the wall material 12. Heptafluoropropane or another suitable propellant gas, such as nitrogen, is preferably used as the propellant 3. The anesthetic reservoir 1 is equipped with a first valve 4, which is shown as a mechanically actuated lifting valve in the FIGURE. The first valve 4 is in flow connection with the pressurized liquid anesthetic reserve 2 and is opened by means of an adapter 5 that can be attached to the mounting element 6 of an anesthesia apparatus. As an alternative, the first valve 4 can be opened by one or more coils on the anesthesia apparatus and the connection between the anesthetic reserve 2 and the anesthesia apparatus can thus be established. The anesthesia apparatus has an anesthetic metering line from the mounting element 6 to the closed respiration system 9 indicated schematically. This metering line contains the following components: A second valve 7, which is in flow connection with the mounting element 6, is adjusted via a measuring and control line 10 as a function of the anesthetic currently being used and as a function of the pressure of the liquid anesthetic, which is measured by means of, e.g., a pressure pickup 11 provided with a piezo element in the anesthetic metering line in front of the second valve 7. The anesthetic is thus metered into the closed respiration system 9 of the anesthesia apparatus by means of a volumetric nozzle 8. The amount metered depends on the pressure of the liquid anesthetic in the anesthetic metering line. The internal pressure in the anesthetic reservoir 1 depends on the temperature, which is determined, e.g., with a prior-art temperature sensor. If the dependence of the amount metered on the pressure and/or the temperature is known, this characteristic can be stored in the measuring and control unit 10, so that the second valve 7 is timed in a correspondingly adapted manner at different measured pressures.

The adapter 5 makes it possible to replace an anesthetic reservoir 1 without anesthetic escaping because the first valve 4 opens only when the anesthetic reservoir 1 is tightly connected to the adapter 5.

The cumbersome refilling and transferring of anesthetics is eliminated by the present invention. An emptied anesthetic reservoir 1 is simply removed from the plug-in socket of the anesthesia apparatus, and instead is replaced with a filled anesthetic reservoir 1. The filling and optionally the reuse of the reservoir are performed under controlled conditions at the anesthetic manufacturer. Due to the possibility of simply and rapidly replacing the anesthetic reservoir 1, different anesthetics can also be used during anesthesia after correspondingly replacing the tanks. Due to the mechanical separation of the propellant 3 from the anesthetic in the reservoir, mixing of the two gases is ruled out. The amount of liquid or the amount of the propellant gas 3 is, of course, selected to be such that the anesthetic can be pressed out of the reservoir without residue.

As an alternative, the separation of the propellant 3 from the anesthetic reserve 2 can also be embodied by means of a mobile piston with sealing elements, but the sealing elements must be resistant to the anesthetic.

Another advantage of the present invention is that the anesthetic is stored in the reservoir, whose first valve 4 opens only when the reservoir is plugged into the plug-in socket of the anesthesia apparatus and completely closes again after removal from the apparatus. Partially used reservoirs that have been removed from the anesthesia apparatus also remain closed until the next use.

The anesthetic reservoir 1 is preferably provided with a code in the form of a transponder or an electronic memory element, which can be read by the anesthesia apparatus and is specific of the anesthetic being used and/or the individual reservoir.

The anesthetic reservoir is especially preferably provided with a filling level sensor, which is designed, e.g., in the form of an electric capacitive resistor element and whose signal is processed in the anesthesia apparatus, and/or in the form of a display or an alarm, which alerts the operating personnel that the reservoir must be replaced.

A heating means for heating the anesthetic may be present in the anesthesia apparatus and especially in the anesthetic metering line between the mounting element 6 and the second valve 7 in order to counteract cooling while large amounts are being removed.

The anesthetics usually used are inhalation anesthetics, especially halothane, enflurane, isoflurane, desflurane, and sevoflurane.

While specific embodiments of the invention have been shown and described in detail to illustrate the application of the principles of the invention, it will be understood that the invention may be embodied otherwise without departing from such principles.

What is claimed is:

1. An anesthetic metering system comprising:
    an anesthesia apparatus with a mounting element a metering line having a connection to a respiration system with a breathing gas flow, having breathing gas flowing therein, the metering line being connected to the breathing gas flow passage for metering anesthetic thereto;
    an anesthetic reservoir with a liquid anesthetic reserve limited by a flexible material wall;
    a propellant applying pressure acting on the liquid anesthetic reserve via the flexible material wall material;
    a first valve element connected to the anesthetic reservoir and in flow connection with the liquid anesthetic reserve, the first valve element being insertable into said anesthesia apparatus mounting element; and
    a volumetric nozzle connected to the metering line for the metered release of the liquid anesthetic to the anesthesia apparatus breathing gas flow passage.

2. An anesthetic metering system in accordance with claim 1, further comprising a measuring and control unit and at least one of a pressure pickup and a temperature sensor wherein the anesthesia apparatus has a second valve in flow connection with the mounting element and actuated via the measuring and control unit as a function of the anesthetic currently being used and as a function of one or both of the pressure measured by means of the pressure pickup in front of the second valve and as a function of the temperature of the liquid anesthetic being used for metering the anesthetic, which is measured by means of the temperature sensor.

3. An anesthetic metering system in accordance with claim 1, wherein the propellant is heptafluoropropane or nitrogen.

4. An anesthetic metering system in accordance with claim 1, wherein the flexible material wall limiting the liquid anesthetic reserve consists of aluminum, polyethylene or a metal-coated flexible plastic laminate.

5. An anesthetic metering system in accordance with claim 1, wherein the first valve is a valve that is opened mechanically or electromagnetically during insertion into the anesthesia apparatus.

6. An anesthetic metering system in accordance with claim 1, wherein the anesthetic reservoir is provided with a code in the form of a transponder or an electronic memory element, which can be read by the anesthesia apparatus and is specific of the anesthetic and/or the anesthetic reservoir.

7. An anesthetic metering system in accordance with claim 1, wherein the anesthetic reservoir is equipped with a filling level sensor for the remaining anesthetic reserve, filling level sensor providing a signal that is processed and/or displayed in the anesthesia apparatus.

8. An anesthetic metering system in accordance with claim 2, wherein the pressure pickup is a piezo crystal pickup.

9. An anesthetic metering system in accordance with claim 1, further comprising a heating means for heating the anesthetic, said heating means being arranged at the anesthesia apparatus.

10. An anesthetic metering device comprising:
    an anesthesia apparatus with a mounting element and a metering line having a connection to a respiration system with a breathing gas flow;

an anesthetic reservoir container with a propellant space and a liquid anesthetic reserve containing a liquid inhalation anesthetic and delimited by a flexible material wall, the flexible material wall separating the liquid anesthetic reserve from the propellant space, the anesthetic reservoir being connectable to and disconnectable from the anesthesia apparatus via mounting in said mounting element;

a propellant disposed in the propellant space applying pressure acting on the liquid anesthetic reserve via the wall material;

a first valve element connected to the anesthetic reservoir and in flow connection with the liquid anesthetic reserve, the first valve element being actuatable upon the anesthetic reservoir being connected into said anesthesia apparatus mounting element; and a volumetric nozzle connected to the metering line for the release of liquid anesthetic to the anesthesia apparatus and into the breathing gas flow of the respiration system.

11. An anesthetic metering device in accordance with claim 10, further comprising a measuring and control unit and at least one of a pressure pickup and a temperature sensor wherein the anesthesia apparatus has a second valve in flow connection with the mounting element and actuated via the measuring and control unit as a function of the anesthetic currently being used and as function of one or both of the pressure measured by means of the pressure pickup in front of the second valve and as a function of the temperature of the liquid anesthetic being used for metering the anesthetic, which is measured by means of the temperature sensor.

12. An anesthetic metering device in accordance with claim 10, wherein the flexible material wall limiting the liquid anesthetic reserve consists of aluminum, polyethylene or a metal-coated flexible plastic laminate.

13. An anesthetic metering device in accordance with claim 10, wherein the first valve is a valve that is opened mechanically or electromagnetically during insertion into the anesthesia apparatus.

14. An anesthetic metering device in accordance with claim 1, further comprising a heater arranged at the anesthesia apparatus.

15. A method of metering an inhalation anesthetic, comprising the steps of:

providing an anesthesia apparatus with a mounting element, a metering line, a closed respiration system with a breathing gas flow, and a volumetric nozzle connected to the metering line for the release of anesthetic to the breathing gas flow of said closed respiration system;

providing an anesthetic reservoir container with a propellant space and a liquid anesthetic reserve delimited by a flexible material wall, the flexible material wall separating the liquid anesthetic reserve from the propellant space and with a propellant disposed in the propellant space applying pressure acting on the liquid anesthetic reserve via the wall material;

providing the reservoir container with a valve element connected to the anesthetic reservoir and in flow connection with the liquid anesthetic reserve, the valve element being actuated, allowing flow of the liquid anesthetic out of the liquid anesthetic reserve, upon the mounting of the reservoir container on the mounting element; and mounting the anesthetic reservoir container to the mounting element to allow liquid anesthetic to flow into said metering line for the release of anesthetic to the breathing gas flow.

16. A method in accordance with claim 15, further comprising:

providing the anesthesia apparatus with a liquid anesthetic metering valve in flow connection with the metering line;

providing a measuring and control unit and at least one of a pressure pickup and a temperature sensor;

actuating the liquid anesthetic metering valve via the measuring and control unit as a function of the anesthetic currently being used and as a function of one or both of the pressure measured by means of the pressure pickup in front of the liquid anesthetic metering valve and as a function of the temperature of the liquid anesthetic being used for metering the anesthetic, which is measured by means of the temperature sensor.

17. A method in accordance with claim 15, wherein the flexible material wall limiting the liquid anesthetic reserve is formed of aluminum, polyethylene or a metal-coated flexible plastic laminate.

18. A method in accordance with claim 15, wherein the valve element is a valve that is opened mechanically or electromagnetically during insertion into the anesthesia apparatus.

19. A method in accordance with claim 15, further comprising heating the liquid anesthetic after or as the liquid anesthetic is being allowed to flow into said metering line.

20. An anesthetic metering system in accordance with claim 1, further comprising a measuring and control unit and at least one of a pressure pickup and a temperature sensor wherein the anesthesia apparatus has a second valve in flow connection with the mounting element and actuated via the measuring and control unit as a function of the anesthetic currently being used and as a function of one or both of the pressure measured by means of the pressure pickup in front of the second valve and as a function of the temperature of the liquid anesthetic being used for metering the anesthetic, which is measured by means of the temperature sensor and wherein the first valve is a valve that is opened mechanically or electromagnetically during insertion of the anesthetic reservoir into the anesthesia apparatus.

* * * * *